US007222260B2

(12) United States Patent
Hellmold

(10) Patent No.: US 7,222,260 B2
(45) Date of Patent: May 22, 2007

(54) TEST SYSTEM FOR MEDICAL SYSTEMS

(75) Inventor: Kurt-Ulrich Hellmold, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 420 days.

(21) Appl. No.: 10/768,914

(22) Filed: Jan. 30, 2004

(65) Prior Publication Data

US 2004/0249575 A1 Dec. 9, 2004

(30) Foreign Application Priority Data

Jan. 30, 2003 (DE) ................................ 103 03 720

(51) Int. Cl.
*G06F 11/00* (2006.01)
(52) U.S. Cl. .......................................... 714/25; 714/32
(58) Field of Classification Search .................. 714/32, 714/25; 378/91
See application file for complete search history.

(56) References Cited

U.S. PATENT DOCUMENTS

| 5,812,397 | A |   | 9/1998 | Pech et al. | |
|---|---|---|---|---|---|
| 5,938,607 | A | * | 8/1999 | Jago et al. | 600/437 |
| 6,212,256 | B1 | * | 4/2001 | Miesbauer et al. | 378/118 |
| 6,230,043 | B1 | * | 5/2001 | Johnson | 600/425 |
| 6,381,557 | B1 | * | 4/2002 | Babula et al. | 702/183 |
| 2004/0107213 | A1 | * | 6/2004 | Zubeldia et al. | 707/104.1 |
| 2004/0120557 | A1 | * | 6/2004 | Sabol et al. | 382/128 |
| 2004/0122706 | A1 | * | 6/2004 | Walker et al. | 705/2 |

FOREIGN PATENT DOCUMENTS

EP 0 858 034 6/2002

* cited by examiner

*Primary Examiner*—Dieu-Minh Le
(74) *Attorney, Agent, or Firm*—Schiff Hardin LLP

(57) ABSTRACT

A test system for a medical system that has a central control unit to control medical system components dependent on received operating commands, has an interface for setting up a data connection to the central control unit, a data storage, and a transmission device that provides a sequence of date packets that correspond to operating commands for controlling the system components, coded for the central control unit of the medical system, according to the specification of a test file readout from the data storage, and for monitored transfer of the sequence of data packets to the central control unit. The present test system allows automated function tests of medical systems to be reproducibly implemented without effort by personnel.

11 Claims, 1 Drawing Sheet

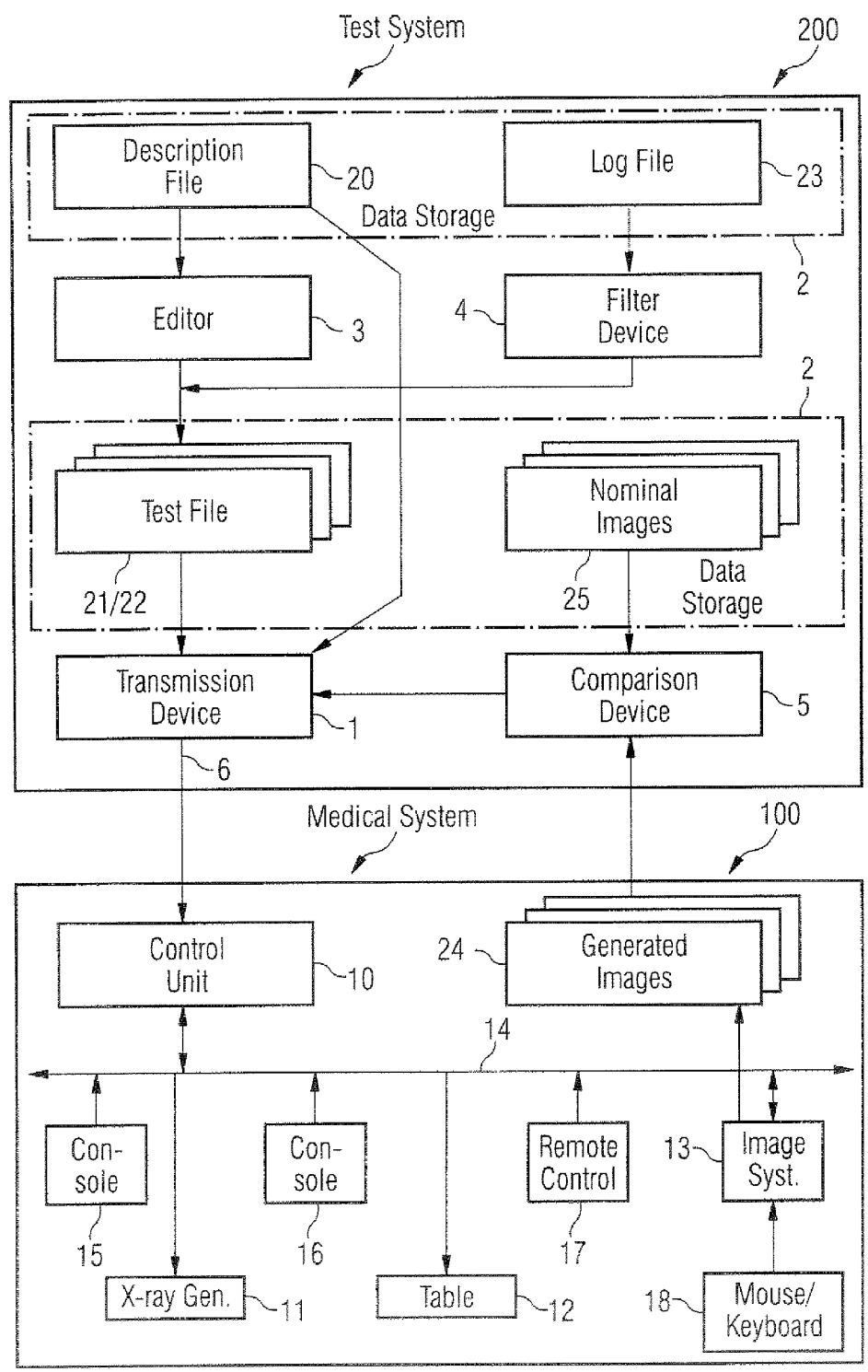

TEST SYSTEM FOR MEDICAL SYSTEMS

BACKGROUND OF THE INVENTION

1. Field of the Invention

The present invention concerns a test system for medical systems of the type having a central control unit to control the system components dependent on received operating commands, in particular for x-ray systems.

2. Description of the Prior Art

In medical diagnostics, different medical systems such as, for example, x-ray systems or magnetic resonance tomography systems are used in order to acquire data from inside the body of a patient. These medical systems must undergo function tests before their delivery to the customer as well as subsequently at specific time intervals, in order to ensure the correct operation. These tests are presently implemented manually using informal test plans. Test procedures are specified that are test cases for all requirements. A test case includes a sequence of individual operation commands that are entered by the tester into the system via operating units in the temporal sequence specified in the test plans. For example, a digital x-ray system normally includes (as operating units for the image system) a keyboard for the input of key codes, as well as a mouse for the input of screen positions, and, for the x-ray system, a generator console for the input of the acquisition parameters as well as a remote control for the input of the primary functions during an examination. The x-ray system has a central control unit that is networked with all system components, receives the corresponding operating commands from the operating units, and controls the individual components dependent on the received operating commands.

Since the functionality of digital x-ray systems continually grows and the test expenditure super-proportionally increases with the number of the functions, the function tests require an ever-greater expenditure. A further problem in the operation of medical systems exists in the reproduction of error situations that occur during the operation at the client. Thus, in x-ray systems, relevant events during the operation are recorded in log files in order to be able to subsequently analyze occurred errors. The log files are interpreted by the tester, who attempts to reproduce the error procedure via manual generation of the events, by entering corresponding operating commands, in order to then generate significant analysis data. This procedure, however, is very complex in terms of personnel.

A device for remote maintenance of a medical system is known from U.S. Pat. No. 6,381,557 that concerns interactivity with the user of the system. Using screen menus, given occurrence of an incident or a disruption the user of the system can contact a service center connected via a network request service. The printout for the implementation of this service, however, includes only the request or the retrieval of data (for example log files or image data) stored in the system over preceding operation, which are subsequently evaluated in the service center in order to detect a possible error or a possible error function. The user of the system is apprised of this in a report that is transmitted back. Dependent on the type of the service request, the service technician involved in the respective cases in the service center actively participate in a different manner in each case. The information necessary for the evaluation can be either transmitted directly to the service center with the service request or can be retrieved upon the request for service by the service center itself via the network.

European Application 0 697 661 concerns a device for technical diagnosis of errors in a medical device. The medical device is fashioned such that the individual components can respectively implement self-tests independently of one another that can be activated by the connected diagnosis device. This device has a first module with a commercial diagnosis software component and a second module that transmits the translation of service commands (that must be input by specialist experts) to the device components to be diagnosed. The error diagnosis ensues by activation of the self-test of the individual components and evaluation of the results of the self-tests as well as further status information.

SUMMARY OF THE INVENTION

An object of the present invention is to provide a test system for medical systems, in particular for x-ray systems, which reduces the expenditure in terms of personnel in the implementation of function tests and provides reproducible results.

The above object is achieved in accordance with the present invention in a test system for a medical system, that has a central unit to control medical system components dependent on received operating commands, wherein the test system has an interface for setting up a data connection to the central control unit, a data storage, and a transmission device that provides a sequence of data packets that correspond to operating commands for controlling the system components, the operating commands being coded for the central control unit of the medical system according to the specification of a test file that is readout from the data storage. The transmission device also monitors transfer of the sequence of data packets to the central control unit of the medical system. All of these procedures are executed automatically by the test system, without the involvement of personnel.

The present test system is fashioned for medical systems that has a central control unit to control system components dependent on received operating commands. It is in particular suited for digital x-ray systems, for example for the systems Iconos and Siregraph with the digital image system Fluorospot Compact by Siemens AG. These systems have a suitable central control unit to control the system components.

The present test system has an Interface for the setup of a data connection to the central control unit, a data storage, and a transmitter device that is fashioned for providing a sequence of data packets that correspond to operating commands to control the system components, coded for the central control unit according to specification of a test file read out from the data storage that has the associated operating commands, and for monitored transfer of the sequence of data packets to the central control unit, with the temporal sequence of the data packets predetermined by the test file (designated below as the test sequence).

For the function test of the system, the present test system is connected directly or via an existing network to the central control unit. This central control unit of the system is networked with all system components and also can receive all operating commands from the additionally connected test system, instead of from typical control units. The image computer of the image system also can receive all local operation events of the keyboard and the mouse via the central control unit, which sends this information to the image system. It is thus possible to generate all operation events via the present test system and to control the system functions from this source.

The present test system enables all operation events that can be generated by the operator of the system via command inputs at the normal operating units to be generated in a freely predeterminable sequence via the test system, and to transmit all operation events to the central control unit. The transfer ensues in the same manner as the transfer of the operation commands by the existing operating units. Each operation event or, respectively, each operating command is represented by an associated data packet that is transmitted to the central control unit of the system. Such a data packet includes a data code, predetermined for the respective operation event (for example a Key stroke of a specific key of the keyboard) that is understood by the central control unit. The central control unit receives these data packets and effects the corresponding commands by controlling the individual system components. Special inputs of a tester for the generation of the individual system procedures according to the test plan predetermined for the system are no longer necessary, since the test system already prepares, monitors, and transfers to the central control unit such test procedures in the necessary real-time sequence. The individual test procedures can be implemented often and at every point in time without effort, for example also automated at night. Due to the exact reproducibility, the test results are precise, neutral and without individual statistical spreading. The individual test cases or test procedures (that are prepared by the transmitting device in connection with the test files) can, without great effort, take into account a number of case differences, such that, for example, the same test cases can be repeated with all image types of an x-ray system. Simple generation and implementation of test cases to check the limit stress of the system, for example via generation of 1000 patient insertions, can also be realized with the test system.

With the present test system, a tool is prepared for test automating in medical systems, in particular in x-ray systems, that enables, by automation of the function test a quality assurance sufficient for present-day requirements. The test system entails no application and consequential costs. Given system changes, no correction of the test cases is necessary as long as the operating logic of the system remains constant. The software of the functions of the image system of the medical system remains unchanged. As warranted, only a second input for the operator events must be achieved at a central location.

In the preferred embodiment of the present test system, an editor is arranged with which a sequence of names of operating commands can be created with a respectively associated time value, and can be stored as a test file in the data storage. The time value associated with each operating command provides the temporal sequence in which the individual operating commands have to be executed, meaning the sequence in which they must be transmitted from the transmitting device to the central control unit. Furthermore, in this embodiment, a description file is provided by means of the data storage that comprises names, identification character strings and associated data packets of the operating commands possible in the x-ray anode. The transmission device has a generator that generates the sequence of data packets to be transmitted to the central control unit according to the specification of the read-out test file via regression to the specification file. The generator searches in the specification file for the names of the respective operating commands given in the test file and transmits the data packets associated with them. The transmission of the data packets to the central control unit via the transmitting device in turn ensues corresponding to the time values specified in the test file, which preferably represent the relative time with regard to the respective preceding event.

Furthermore, the present test system can include a filter device to create a test file that is fashioned to read in a log file stored in a data storage; to extract data about point-in-time and identification character sequence or names of executed operating commands from the log file; and to create and store a sequence of the executed operating commands—with names, identification character sequence or as a data packet—with a respectively associated time value that corresponds to the temporal sequence of the executed operating commands. This test file is then in turn read out by the transmitter device, and the sequence of operating commands is transmitted to the central control unit as a sequence of data packets in the specified temporal sequence. The sequence of data packets is either directly read out from this test file or in turn generated via regression to the description file in which the data packets are associated with the individual names and identification character sequences of operating commands. The reproduction of error situations in client (customer) systems is enabled via this embodiment. The relevant events that are registered in the log file are thereby filtered, such that the automatic reproduction of the error situation using these log files can in many cases effectively support the error analysis.

Naturally, the present test system can also be realized in a simpler embodiment without the editor and the filter device. In this case, the data storage has a number of test files that already include predetermined test procedures in the form of a sequence of data packets with associated time values. The transmitter device reads in only the test files selected by an operator (via a corresponding selection device, for example via a screen menu) and transmits to the central control unit the data packets included therein, corresponding to the predetermined temporal sequence.

The editor as well as the transmission device preferably are fashioned such that additional monitoring structures or monitoring commands are generated with the editor that recognize and corresponding take into account the transmission device. Such monitoring structures can be, for example, commands for the transmission device for repetition, for conditional interruption, or for skipping over individual sections of the test file. The sequence of data packets to be transmitted to the central control unit can be very variably arranged via these monitoring structures. Given the implementation of a suitable comparing device in the system, with which data or images of the system generated in the test procedure are automatically compared with predetermined nominal data or nominal images, the test procedure can be controlled dependent on the result. Furthermore, a storage device preferably is provided for the storage of the results or images for documentation generated in the test procedure.

In the preferred embodiment of the present test system, event sequences or command sequences can be generated with the editor and the filter device from artificial events (the test cases created with the editor) or from natural events (the filtered log files). The event specification is independent of the physical system structure, since only the logical structure of the events or the hierarchy or parallelism is predetermined. The events of the test procedure can be documented via screen and data dumps and automatically evaluated by the comparison device.

DESCRIPTION OF THE DRAWINGS

The FIGURE is a schematic illustration of an embodiment of the test system of the invention, as an example for testing an x-ray system, with the test system connected to the central control unit of the x-ray system.

DESCRIPTION OF THE PREFERRED EMBODIMENTS

An x-ray system 100 has a central control unit 10, which is connected with the individual system components via a network 14. The central control unit 10 receives operating commands in the form of data packets via the network 14 and controls the individual components of the system via the network 14, corresponding to the received operating commands. In the FIGURE, an x-ray generator 11, a patient table 12 and an image system 13 are shown as components of the x-ray system 100. The operation of this x-ray system 100 by operating personnel ensues via inputs at a generator console 15 for operating the generator 11, at the table console 16 for operating the patient table 12, via mouse or keyboard 18 for operation of the image system 13, or via a remote control 17. Via the last cited operating unit, the operator can input (by pressing corresponding buttons or, as in the image system, via a menu navigation with mouse or keyboard) corresponding operating commands that are supplied as data packets via the network 14 to the central control unit 10.

For automatic function testing of this x-ray system, the central control unit 10 in this example is connected with a test system 200 shown as an example in the FIGURE. The test system 200 includes a transmission device 1 with an interface 6 (indicated in the FIGURE as an arrow for the data transmission) to connect to the central control unit 10. The transmission device 1 serves to prepare a sequence of data packets that represent a test procedure with a sequence of operating commands in predetermined temporal succession, as well as for temporally monitored transmission of this sequence of data packets to the central control unit 10. The central control unit 10 receives the data packets in the same format as the connected operating units. An image computer of the image system 13 also can receive the corresponding operating commands not only via the mouse and keyboard 18, but also from the central control unit 10 via the network 14. It is thus possible to generate all operator events from the test system 200, and therewith to control the x-ray system 100. The transmission device 1 takes over the procedure control for transmission of the data packets.

The test system furthermore has an editor 3, via which an operator can generate a sequence of operating commands and store the sequence as a file in the data storage 2 of the test system 200. With the editor 3, the command or event names can be easily selected in the x-ray system 100 and combined into a corresponding test sequence. A time value that provides the point-in-time of execution of the operating command is added to each selected operating command. The result describes the test case and is stored in a test file 21 under an arbitrary name. In this manner, a number of test files 21 can be stored in the data storage 2 that represent different test cases, i.e. different command or event sequences. Alternatively, an event sequence can be extracted from the log file 23 of a client system (that is copied in the data storage 2) using a filter device 4. In such a log file 23, the operation events that have occurred are recorded with the associated number (generally designated in the present patent application as an identification character sequence) and the point-in-time of their execution.

The transmission device 1 reads the test sequences generated by the editor 3 or the filter device 4 from the selected test file 21 and, corresponding to the designated timing, transmits the data packets associated with the operating commands to the central control unit 10 for processing. The data packets associated with the individual operating events or operating commands are read out by the transmission device 1 from an event specification file 20 in which all operating events or operating commands of the x-ray system are defined, and which contains the name, number and the associated data packet.

Alternatively, test files 22 can be stored in the data storage 2 that already contain a sequence of data packets with associated time values. In this case, no description file 20 is necessary.

The test system shown in this example furthermore has a comparison device 5 with which a comparison between nominal and real displays of the image system 13 is undertaken, and an automatic result monitoring is implemented. Images 24 of the image system (real values) generated by the monitor of the image system 13 upon implementation of the respective test run are stored as screen dumps and compared with nominal images 25 likewise stored as screen dumps. The comparison device 5 thus provides information about the result of the comparison. Furthermore, validated real results can be adopted as nominal results in the data storage 2 of the test system.

In the shown embodiment of the present test system, operating commands or operating events are described in a logical structure in a file (the description file), preferably in a standard format. With the editor 3 structured corresponding to this logic, command sequences can be generated in turn in the standard format. Alternatively, log files for generation of the test sequences can be filtered by the filter device 4, and the result stored as a test file. A transmission device structured corresponding to the test sequences is fashioned to handle the monitoring structure, in order to convert (using the description file) the command or event names or numbers into data packets coded for the control unit 10, and to transmit these data packets to the x-ray system 100. With the present test system 200, a function test of an x-ray system 100 or another suitably fashioned medical system can be automatically implemented without effort by personnel effort.

Although modifications and changes may be suggested by those skilled in the art, it is the intention of the inventor to embody within the patent warranted hereon all changes and modifications as reasonably and properly come within the scope of his contribution to the art.

I claim as my invention:

1. A test system for a medical system, said medical system comprising a plurality of medical system components, including a medical imaging system, and a central control unit connected to said medical system components for controlling said medical system components dependent on operating commands, said test system comprising:

an interface adapted to produce a data connection to the central control unit of the medical system;

a data storage containing at least one test file, said test file containing specifications for conducting a function test of the medical system, that includes a function test of said medical imaging system, said test file representing operating commands with respectively associated time values that define a temporal sequence of said operating commands for executing said test function, including defined chronological spacings between said operating commands; and a transmission device connected to said interface and having access to said test file in said data storage, said transmission device, upon retrieval of said test file from said data storage, generating a sequence of data packets respectively causing non-manual execution of said operating commands for automatically controlling the medical system components, including said medical imaging system, according to the specifications in said test file, said operating commands being coded for said central control unit, and said transmission device monitoring transfer of said sequence of data packets via said interface to said central control unit according to said temporal sequence.

2. A test system as claimed in claim 1 comprising an editor for generating said test file as a sequence of names of operating commands each having a time value, in said temporal sequence, associated therewith, and for causing said test file to be stored in said data storage, and wherein said data storage comprises a description file containing names, identification character strings and associated data packets for said operating commands, and wherein said transmission device generates said sequence of data packets according to the specifications of the test file via regression to said description file.

3. A test system as claimed in claim 2 wherein said editor generates monitoring commands for said transmission device and includes said monitoring commands in said test file.

4. A test system as claimed in claim 1 wherein said data storage contains a plurality of test files each having a different predetermined sequence of data packets with respectively associated time values in said temporal sequence.

5. A test system as claimed in claim 1 wherein said data storage contains a log file containing points-in-time and an identification, selected from the group consisting of identification character sequences and names, of operating commands that have been executed by said medical system, and a filter device connected to said data storage for retrieving and reading said log file and for generating said test file therefrom as a sequence of said identification and said data packets with respectively associated time values in said temporal sequence, and causes said test file to be stored in said data storage.

6. A test system as claimed in claim 1 wherein said test file stored in said data storage contains monitoring commands selected from the group consisting of condition-dependent interruptions, condition-dependent jumps, and condition-dependent repetitions.

7. A test system as claimed in claim 1 comprising a user-operable selection device in communication with said transmission device for causing said transmission device to readout a test file selected by a user.

8. A test system as claimed in claim 1 wherein said medical system generates test results, after executing said function test specified by said test file, said test results comprising at least one of data and images, and wherein said test system comprises a comparison device, having access to said test results, for comparing said test results to stored nominal test results, and for generating an output dependent on the comparison.

9. A test system as claimed in claim 1 comprising a storage device for storing said test results.

10. A test system as claimed in claim 1 wherein said test transmission device and said data storage are integrated into said control device of said medical system.

11. A test system as claimed in claim 1 wherein said interface is adopted to allow said transmission device to communicate with said control device via a network of said medical system.

* * * * *